United States Patent [19]
Lindsay et al.

[11] Patent Number: 5,843,203
[45] Date of Patent: Dec. 1, 1998

[54] AGRICULTURAL CARRIER

[75] Inventors: A. David Lindsay, Brunswick; Barry A. Omilinsky, Princeton Junction, both of N.J.

[73] Assignee: GranTek, Inc., Granger, Ind.

[21] Appl. No.: 620,937

[22] Filed: Mar. 22, 1996

[51] Int. Cl.⁶ .......................... A01N 25/02; A01N 25/08; A01N 27/00
[52] U.S. Cl. ............... 71/23; 71/904; 71/DIG. 1
[58] Field of Search .................. 264/117; 71/11, 71/23, 904, DIG. 1

[56] References Cited

U.S. PATENT DOCUMENTS

| | | | |
|---|---|---|---|
| 4,291,052 | 9/1981 | Gillings et al. | 514/465 |
| 4,338,297 | 7/1982 | Michael et al. | |
| 4,560,527 | 12/1985 | Harke et al. | 264/117 |
| 4,563,344 | 1/1986 | Kotz et al. | 424/17 |
| 4,621,011 | 11/1986 | Fleischer et al. | |
| 4,631,301 | 12/1986 | Kozuma et al. | |
| 4,696,822 | 9/1987 | Matsumura et al. | 424/490 |
| 4,808,615 | 2/1989 | Ott et al. | |
| 5,019,564 | 5/1991 | Lowe et al. | 514/75 |
| 5,118,506 | 6/1992 | Eichoefer | 424/196.1 |
| 5,310,721 | 5/1994 | Lo | 504/116 |

Primary Examiner—Jan H. Silbaugh
Assistant Examiner—Kenneth M. Jones
Attorney, Agent, or Firm—Laff Whitesel Conte & Saret Ltd.

[57] ABSTRACT

An improved agricultural carrier and a method of making the carrier is disclosed. The granular carrier is adapted for carrying a low-melting chemical, specifically pesticides. An aromatic solvent is used to dissolve the low-melting chemical, before combining it with the carrier. The granular carrier unexpectedly exceeds its liquid holding capacity for the low-melting chemical.

5 Claims, No Drawings

AGRICULTURAL CARRIER

BACKGROUND OF THE INVENTION

Agricultural granules are well known to the agricultural crop and horticultural industries. Indeed, since its inception in the late 1940's, the agricultural granule form of pesticide formulary has become the most widely used and most versatile of the available pesticide delivery systems. In these systems, the granules act as carriers for the pesticides. The large number of particles per unit weight of the granules allows the granules to be applied per unit area at a rate which is toxic to the pest but which will not cause damage to desirable life forms. To those individuals knowledgeable in pesticide formulary, an agricultural granule used as a diluent is defined as a material which has an adequate sorptive capacity and which is chemically inert.

An agricultural granule which is to be used as a carrier must be capable of carrying pesticide to the pest-control site without any significant losses of the pesticide and then releasing the pesticide for control. For the agricultural granule carrier to be effective, it must have an adequate liquid holding or sorptive capacity and it must be generally free-flowing. Typical sorptive agricultural granules were derived in the past from materials such as clay, corn cob, vermiculite, rice hulls, and pumice and comprised distinct particles within the range of 4 to 80 mesh (U.S. Standard). Such agricultural granules have many advantages, including ease of application with accurate control of rate and placement, and ease of handling and transport.

Recently, agricultural granules formed from natural plant fiber or paper sludge have been developed. Although such granules have many highly desirable characteristics and are widely used as a diluent, in certain applications they are limited by their sorptive capacity. That is, in certain applications it has been found that such granules cannot carry as much pesticide per unit mass to the site of control as desired. To overcome this, it is necessary to increase the absorptive capacity of these plant-fiber granules.

SUMMARY OF THE INVENTION

In keeping with one aspect of the invention, an improved agricultural granular carrier comprised of 10–100% plant fibers and 0–90% mineral filler, and a low-melting pesticide combined with an aromatic solvent is disclosed. The improved carrier is preferably comprised of about 30% plant fibers and about 70% mineral filler and formed by an agglomeration method.

The low-melting pesticide preferably has a melting point between about 30° C. and about 60° C. and may be selected, for example, from the group consisting of chlorpyrifos, trifluralin, pendimethalin, bifenthrin, cypermethrin, and tefluthrin.

The aromatic solvent may be selected from the group consisting of Aromatic 150, Chemical Abstract Service (CAS) Registry No. 64742-94-5; Aromatic 200, naphthalene depleted, CAS Registry No. 64742-94-5; Aromatic 100, CAS Registry No. 64742-95-6; and HAN 857, CAS Registry No. 64742-06-9. The ratio of the low-melting chemical to the solvent is between about 60:40 and about 90:10, preferably between about 62:38 and 80:20, more preferably between 64:36 and 76:24, and most preferably at 70:30.

In keeping with another aspect of the invention, a method of making an improved agricultural granular formulation with a low-melting pesticide selected from the group consisting of pesticides in excess of the carrier's apparent liquid holding capacity is disclosed.

The method uses the steps of selecting an aromatic solvent, adding the low-melting pesticide to the aromatic solvent to form a solution and applying the solution to granules which are adapted for carrying the pesticide.

In keeping with yet another aspect of the invention, an improved agricultural carrier comprised of a granular carrier, chlorpyrifos, and an aromatic solvent is disclosed.

DETAILED DESCRIPTION OF THE INVENTION

The present invention involves applying a combination of a low-melting pesticide with an aromatic solvent to agglomerated cellulosic carrier granules in an amount which exceeds the known liquid-holding capacity of the carrier granules. Notwithstanding this application in excess of the liquid holding capacity, the granules retain their shape and remain free-flowing.

Preferred carrier granules are agglomerated cellulosic granules sold by Edward Lowe Industries under its trademark BIODAC®. Methods of agglomeration are disclosed, for example, in U.S. Pat. No. 4,560,527. These and other agglomerated granules preferably contain at least 30% by weight of cellulosic fibers. BIODAC® 8/30, 12/20, 16/30, 20/40, and 30/50, in which the numbers represent the U.S. mesh size of the two screens used are all known to work in this application.

The melting point range for pesticides to which this invention is applicable is approximately 30° C. to 60° C. Such pesticides include, for example, chlorpyrifos (melting point 41°–42° C.), trifluralin (melting point 49° C.), pendimethalin (melting point 54°–58° C.), bifenthrin (melting point 59°–64° C.), cypermethrin (melting point 60°–80° C.), and tefluthrin (melting point 45° C.). Other pesticides with melting points in this range may be used in various applications.

Any typical aromatic hydrocarbon solvent can be used. Among these are, for example, solvents available from Exxon Chemical and sold under the names of: Aromatic 150, Chemical Abstract Service (CAS) Registry No. 64742-94-5; Aromatic 200, naphthalene depleted, CAS Registry No. 64742-94-5; Aromatic 100, CAS Registry No. 64742-95-6; and HAN 857, CAS Registry No. 64742-06-9. Other suitable aromatic solvents are available from Koch Chemical, Mobil Chemical, Ashland, Amoco, and Texaco.

A preferred weight ratio of the pesticide to the carrier granule is about 15:85. Greater ratios of pesticide to carrier are desirable but typically at ratios greater than about 18:72 the granules are too wet and stick together. Unexpectedly, combining the pesticide with an aromatic solvent increases the apparent liquid holding capacity of the carrier. In one preferred embodiment of the invention, the weight ratio of pesticide/aromatic solvent to carrier is between about 19.4:80.6 to 24:76 and most preferably at about 22:88.

It is believed that the combination of the large interstitial spaces of the carrier granules with the low melting point chemicals is important in this treatment, resulting in an unexpected increase in the liquid holding capacity of the granules. When a liquid is added to granules, it usually flows freely in and out of the spaces. When a low melting chemical is present in the liquid, it is believed that the chemical tends to crystallize in the interstitial spaces. The granules can thus hold more liquid which contains low melting point chemicals than liquid without such chemicals.

The treated granules which are impregnated with the chemical have several applications. The granules may be mixed with seeds and then planted, or spread across lawns or prepared fields. Or, the granules may be spread in other areas, such as chicken houses or dog pens, where the continued release of the pesticides is important. Rain, irrigation and physical-chemical phenomena will gradually release the chemical to be taken up by the targeted plant or pest.

The following examples illustrate the present invention in a manner by which it can be practiced but, as such, should not be construed as limitations upon the overall scope of the invention.

EXAMPLES

In the present application, 15:85 w/w (herbicide or pesticide: carrier) is preferred. Although the target value is optimally 15% w/w, some overage of the technical is desirable. The overage is to allow for possible errors including formulation errors, variability in the manufacturing process, or assay problems. The present work used a 3% overage, or a calculated 15.5% w/w (103% of 15 percent).

Most pesticides are not used agronomically in an absolutely pure form. For instance, technical grade chlorpyrifos runs at about 98% purity. Thus, for the carrier to achieve 15.5% chlorpyrifos (15% with a 3% overage), the blend would need to be 15.8% w/w (technical chlorpyrifos/carrier) 15.5%/0.98). Because chlorpyrifos is a solid at normal, ambient temperatures, it has to be melted or dissolved before it can be applied to the granules. Once the technical has melted, one must deal with its high viscosity and its tendency to readily crystallize as it cools. Therefore, it is preferable to dissolve it and to use it in a solution form for economical delivery to the granules. This dilution of the pesticides, while simplifying the application process, increases the total amount of liquid to be placed onto the granules for a given concentration of chlorpyrifos.

Example 1

When the apparent liquid holding capacity of the agglomerated cellulosic granules is exceeded, the individual particles of the carriers are no longer free-flowing, but instead become a wet mass which will not flow. The loss of flowability means that the wet mass of carrier cannot be applied using conventional application equipment and techniques.

The cellulosic particles used in this example had apparent liquid holding capacity averaging 18% w/w (18 g liquid: 82 g cellulosic particles). When 18 grams of liquid, including aromatic solvents listed above, were added to 84 grams of cellulosic granules the granules became a wet mass which would not flow.

Example 2

In this example, technical grade chlorpyrifos was added in a 90% w/w solution, so that the target liquid holding capacity would be 17.2% w/w. (This number is calculated by dividing 15.5 by 0.9.) However, when a 90% solution was added to cellulosic granules in this ratio, the 15.5% w/w granular was unsatisfactory. Although these granules looked dry, the impregnated granules caked on standing and had surface crystals.

Example 3

In this example, when a 60% w/w solution of chlorpyrifos was added to cellulosic granules at 25.8% w/w (that is still 15.5% w/w chlorpyrifos/cellulosic granules), another unsatisfactory granule which was wet and did not dry on standing resulted.

Example 4

Unexpectedly, it was found that a 70% w/w chlorpyrifos solution in Aromatic 150 could be applied to cellulosic granules at 22.1% w/w (considerably more than the expected liquid holding capacity of 18% of the cellulosic granules) to form satisfactory granules. The granules were free-flowing within minutes, and no crystals formed on the surface. The granules retained these desirable characteristics even after storage of 0° C. or 50° C., or being initially stored at 50° C. for one week and then being placed at 0° C. for one week.

Example 5

A control using Aromatic 150 alone confirmed that exceeding the expected liquid holding capacity of the cellulosic granules of 18% w/w and loading them to 22% w/w resulted in a wet, non-flowing mass. It remained non-flowing after 24 hours.

Table 1 summarizes the ratios tested, including ratios not specifically discussed above. In all examples, chlorpyrifos was dissolved in an aromatic solvent, Aromatic 150, at the indicated ratios and applied in an amount sufficient to produce 15.5% w/w chlorpyrifos granules.

TABLE 1

| Loading Level of Variables (Chlorpyrifos and Solvent) % w/w | Ratio Chlorpyrifos: Solvent | Solvent | Granular | Granular Characteristics |
| --- | --- | --- | --- | --- |
| 15.8% | 100:0 | pesticide | Biodac 12/20, 16/30, 20/40, HLG | Spraying melted chlorpyrifos onto Biodac results in a sticky granular with surface crystals. |
| 17.2% | 90:10 | Aromatic 150 | Biodac 12/20 | Dry, cakes on standing, surface crystals. |
| 19.4% | 80:20 | Aromatic 150 | Biodac 12/20 | Initially free flowing, but cakes on standing. |
| 20.4% | 76:24 | Aromatic 150 | Biodac 12/20 Biodac 20/40 | Free flowing |

TABLE 1-continued

| Loading Level of Variables (Chlorpyrifos and Solvent) % w/w | Ratio Chlorpyrifos: Solvent | Solvent | Granular | Granular Characteristics |
|---|---|---|---|---|
| 22.1% | 70:30 | Aromatic 150 | Biodac 12/20, 16/30, 20/40, HLG | Free flowing |
| 24.2% | 64:36 | Aromatic 200 (naphthalene depleted) | Biodac HLG | Free flowing |
| 25.8% | 60:40 | Aromatic 150 | Biodac 12/20 | Wet, non-flowing mass. |
| 22% | 0:100 | Aromatic 150 | | Wet, non-flowing mass. |

Example 6

Aromatic 200, naphthalene depleted, was also used in place of Aromatic 150. At 70:30 w/w (chlorpyrifos: solvent), treated Biodac 12/20 remained free flowing and without surface crystals.

While the present invention has been described with reference to a preferred embodiment thereof, various changes and modifications can be made by those skilled in the art without departing from the spirit and scope of the present invention; therefore, the appended claims are to be construed to cover equivalent structures.

What is claimed is:

1. An improved agricultural carrier comprising:
   a granular carrier adapted for carrying a low-melting chemical with a melting point between about 30° C. and about 60° C. while remaining free-flowing, the carrier comprising 10–100% plant fibers and 0–90% of a mineral filler; and
   the low-melting chemical, combined with an aromatic solvent, present in the granular carrier in an amount exceeding the appairent liquid holding capacity of the carrier,
   wherein the ratio of the low-melting chemical to the solvent is between about 62:38 and about 80:20.

2. The improved agricultural carrier as claimed in claim 1 where the carrier comprises about 30% fibers and about 70% mineral filler.

3. The improved agricultural carrier as claimed in claim 1 wherein the granule is formed by an agglomeration method.

4. The improved agricultural carrier of claim 1 wherein the chemical is selected from the group consisting of chlorpyrifos, trifluralin, pendimethalin, bifenthrin, cypermethrin, and tefluthrin.

5. The improved agricultural carrier of claim 1 wherein the aromatic solvent is selected from the group consisting of Aromatic 150, Chemical Abstract Service (CAS) Registry No. 64742-94-5; Aromatic 200, naphthalene depleted, CAS Registry No. 64742-94-5; Aromatic 100, CAS Registry No. 64742-95-6; and HAN 857, CAS Registry No. 64742-06-9.

* * * * *